United States Patent [19]

Bugelski et al.

[11] Patent Number: 5,455,247
[45] Date of Patent: Oct. 3, 1995

[54] METHODS FOR THE TREATMENT OF HYPERLIPIDEMIA USING AZASPIRANES

[75] Inventors: Peter J. Bugelski, Philadelphia; William D. Kerns, West Chester, both of Pa.

[73] Assignee: SmithKline Beecham Corporation, Philadelphia, Pa.

[21] Appl. No.: 211,881

[22] PCT Filed: Oct. 15, 1992

[86] PCT No.: PCT/US92/08786

§ 371 Date: Apr. 22, 1994

§ 102(e) Date: Apr. 22, 1994

[87] PCT Pub. No.: WO93/07871

PCT Pub. Date: Apr. 29, 1993

[30] Foreign Application Priority Data

Oct. 25, 1991 [GB] United Kingdom ............ 9122721

[51] Int. Cl.⁶ .......... A61K 31/395; A61K 31/55; A61K 31/53; A61K 31/50; A61K 31/495; A61K 31/505; A61K 31/41; A61K 31/415; A61K 31/40

[52] U.S. Cl. .......... 514/278; 514/210; 514/211; 514/212; 514/218; 514/241; 514/242; 514/247; 514/252; 514/255; 514/256; 514/359; 514/383; 514/385; 514/403; 514/409; 514/824

[58] Field of Search ............... 514/210, 211, 514/212, 218, 241, 242, 247, 252, 255, 256, 278, 359, 383, 385, 403, 409, 824

[56] References Cited

U.S. PATENT DOCUMENTS 4,963,557 10/1990 Badger et al. ................ 514/278

Primary Examiner—Kimberly R. Jordan
Attorney, Agent, or Firm—Wayne J. Dustman; Stephen Venetianer; Edward T. Lentz

[57] ABSTRACT

Invented is a method of treatment of hyperlipidemia, in a mammal, including a human, in need thereof which comprises administering to such mammal an effective therefor amount of a substituted azaspirane.

12 Claims, No Drawings

METHODS FOR THE TREATMENT OF HYPERLIPIDEMIA USING AZASPIRANES

This application is a 371 of PCT/US 92/08786 filed Oct. 5, 1992.

This invention relates to a method of treatment of hyperlipidemia in a mammal, including a human, in need thereof which comprises administering to such mammal an effective therefor amount of a substituted azaspirane.

BACKGROUND OF THE INVENTION

Badger et al. U.S. patent application Ser. No. 07/712,325 filed on Jun. 7, 1991, (Badger I) discloses compounds of the formula

in which: m is 1 or 2; $R^1$ and $R^2$ are the same or different and are selected from hydrogen or straight or branched chain alkyl, provided that the total number of carbon atoms contained by $R^1$ and $R^2$ when taken together is 4–10; or $R^1$ and $R^2$ together form a cyclic alkyl group containing 3–7 carbon atoms; A is absent or present as $C_1$–$C_7$ alkyl; and $R^3$ is a heterocyclic or heterobicyclic ring, said heterocyclic or heterobicyclic ring thereby containing up to 10 carbon atoms and from 1–3 heteroatoms of the formula >$NR^4$, where $R^4$ is absent or present as hydrogen, or a straight chain alkyl containing 1–3 carbon atoms; or a pharmaceutically acceptable salt, hydrate or solvate thereof.

Badger (I) does not disclose or claim compounds of Formula (I) as antihyperlipidemic agents.

SUMMARY OF THE INVENTION

This invention relates to a method of treatment of hyperlipidemia in a mammal, including a human, in need thereof which comprises administering to such mammal an effective therefor amount of a compound of the formula

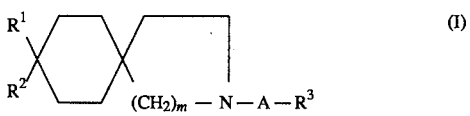

in which:

m is 1 or 2;

$R^1$ and $R^2$ are the same or different and are selected from hydrogen or straight or branched chain alkyl, provided that the total number of carbon atoms contained by $R^1$ and $R^2$ when taken together is 4–10; or $R^1$ and $R^2$ together form a cyclic alkyl group containing 3–7 carbon atoms;

A is absent or present as $C_1$–$C_7$ alkyl; and $R^3$ is a heterocyclic or heterobicyclic ring, said heterocyclic or heterobicyclic ring thereby containing up to 10 carbon atoms and from 1–3 heteroatoms of the formula >$NR^4$, where $R^4$ is absent or present as hydrogen, or a straight chain alkyl containing 1–3 carbon atoms;

or a pharmaceutically acceptable salt, hydrate or solvate thereof.

DETAILED DESCRIPTION OF THE INVENTION

The term "hyperlipidemia" as used in the specification and in the claims is meant the presence of an abnormally high level of lipids in the blood.

The term "antihyperlipidemic" as used herein is meant the lowering of excessive lipid concentrations to desired levels.

Preferred lipids, of which high levels thereof are treated by the presently invented methods, are; cholesterol, triglycerides and low-density lipoproteins.

The preparation of the compounds of Formula (I) and pharmaceutically acceptable salts, hydrates and solvates and formulations thereof is disclosed in U.S. patent application Ser. No. 07/712,325, filed Jun. 7, 1991 the entire disclosure of which is hereby incorporated by reference.

The compounds of this invention are prepared by procedures described here below and illustrated by the examples. Reagents, protecting groups and functionality of the molecule must be consistent with the proposed chemical transformations. Steps in the synthesis must be compatible with the functional groups and the protecting groups.

Formula (I) compounds are prepared as described in Scheme I where $R^1$, $R^2$, $R^3$ and A are as defined in Formula I and the definition of $R^3$ additionally comprises protecting groups, preferably benzyl protecting groups, which are dissociated to prepare the substituents of $R^3$ as defined in Formula (I) or are dissociated and further reacted to prepare the substituents of $R^3$ as defined in Formula (I).

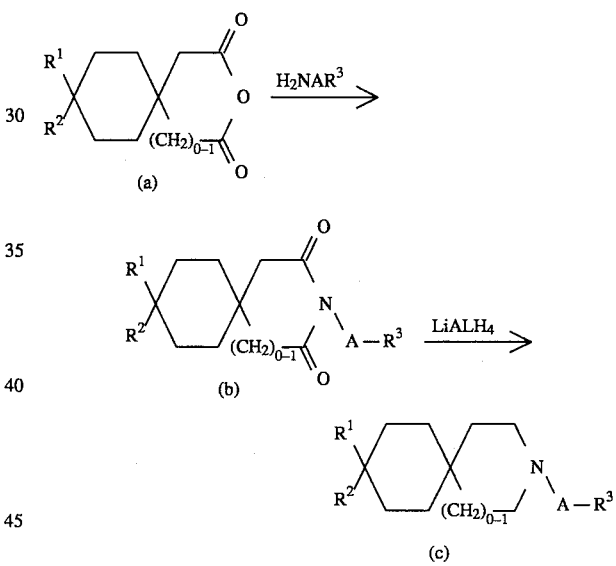

SCHEME I

Scheme I depicts formation of Formula (I) compounds. The starting anhydride compounds are known and are synthesized from available precursors using known procedures. According to Scheme I, a solution of an anhydride Compound (a) and a substituted primary amine compound are added to an appropriate organic solvent, preferably xylene or toluene, to form a reaction mixture. This reaction mixture is stirred at reflux with constant water removal, and evaporated to form formula (b) compounds.

Formula (c) compounds are prepared by adding to a formula (b) compound dissolved in a suitable organic solvent, such as tetrahydrofuran (THF), a suitable reducing agent, preferably, lithium aluminum hydride.

Pharmaceutically acceptable salts and their preparation are well known to those of skill in the art. Preferred pharmaceutically acceptable salts for basic compounds of Formula (I) include, but are not limited to, hydrochloride, citrate, maleate, lactate, hydrobromide, and sulfate.

The compounds of Formula (I) may form hydrates or solvates. It is known to those of skill in the art that charged compounds form hydrated species when lyophilized with water, or form solvated species when concentrated in a solution with an appropriate organic solvent.

A preferred compound of Formula (I), as used herein, is the compound where $R^1$ and $R^2$ are propyl, m is 1, A is absent, and $R^3$ is 4-piperidine which is 8,8-dipropyl-2-azaspiro[4,5]decane-2-(4-piperidine).

This invention discloses compounds of Formula (I) and pharmaceutically acceptable salts or hydrates or solvates thereof as being useful for treatment of hyperlipidemia in a mammal, including humans, in need of such treatment.

The method of this invention of treating hyperlipidemia comprises administering to a mammal, including humans, in need thereof an effective therefor amount of a compound of Formula I.

An effective antihyperlipidemic amount of a compound of Formula (I) or a pharmaceutically acceptable salt or hydrate or solvate thereof (i.e. active ingredient) is useful in treating, prophylactically or therapeutically, any disease state in a mammal, including a human, which is exacerbated or caused by excessive lipid levels. These disease states include hyperlipidemic syndromes, atherosclerosis and transplant arteriolosclerosis. Particularly preferred is the disease state of atherosclerosis.

This invention relates to a method of treatment of hyperlipidemia, in a mammal, including a human, in need thereof which comprises administering an effective therefor amount of a compound of Formula (I) or a pharmaceutically acceptable salt or hydrate or solvate thereof. A compound of Formula (I) or a pharmaceutically acceptable salt or hydrate or solvate thereof can be administered to such mammal, including a human, in a conventional dosage form prepared by combining a compound of Formula (I) or a pharmaceutically acceptable salt or hydrate or solvate thereof, with a conventional pharmaceutically acceptable carrier or diluent according to known techniques, such as those described in Badger (I) U.S. application Ser. No. 07/712,325 filed on Jun. 7, 1991.

It will be recognized by one of skill in the art that the form and character of the pharmaceutically acceptable carrier or diluent is dictated by the amount of active ingredient with which it is to be combined, the route of administration and other well-known variables. A compound of Formula (I) or a pharmaceutically acceptable salt or hydrate or solvate thereof is administered to a mammal, including a human, in need of antihyperlipidemic activity in an amount sufficient to lower lipid concentration to desired levels.

The route of administration of the Formula (I) compound is not critical but is usually oral or parenteral, preferably oral. The term parenteral as used herein includes intravenous, intramuscular, subcutaneous, intranasal, intrarectal, transdermal, intravaginal or intraperitoneal administration. The subcutaneous and intramuscular forms of parenteral administration are generally preferred. The daily parenteral dosage regimen will preferably be from about 0.01 mg/kg to about 10 mg/kg of total body weight, most preferably from about 0.1 mg/kg to about 1 mg/kg. The daily oral dosage regimen will preferably be from about 0.01 mg/kg to about 10 mg/kg of total body weight.

Preferably, each parenteral dosage unit will contain the active ingredient in an amount of from about 0.1 mg to about 100 mg. Preferably each oral dosage unit will contain the active ingredient in an amount of from about 0.1 mg to about 100 mg.

The compounds of Formula (I) which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavoring or coloring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

While it is possible for an active ingredient to be administered alone, it is preferable to present it as a pharmaceutical formulation.

It will be recognized by one of skill in the art that the optimal quantity and spacing of individual dosages of a compound of Formula (I) or a pharmaceutically acceptable salt or hydrate or solvate thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt or hydrate or solvate thereof given per day and duration of therapy can be ascertained by those skilled in the art using conventional course of treatment determination tests.

In addition, the compounds of the present invention can be co-administered with further active ingredients, such as other compounds known for the treatment of elevated lipid levels such as acyl-CoA: Cholesterol acyltransferase (ACAT) inhibitors, HMGCoA reductase inhibitors and bile acid sequestrants.

Without further elaboration, it is believed that one skilled in the art can, using the preceding description, utilize the present invention to its fullest extent. The following examples are, therefore, to be construed as merely illustrative and not a limitation of the scope of the present invention in any way.

I. SYNTHETIC EXAMPLES

In the following Examples, temperature is in degrees Centigrade (°C.).

4,4-Dipropyicyclohexane-1-carboxy-1-acetic acid anhydride, 4,4-diethylcyclohexane-1-carboxy-1-acetic acid anhydride, 4,4-dipropylcyclohexane-1,1-diacetic acid anhydride, and 4,4-diethylcyclohexane-1,1-diacetic acid anhydride were synthesized as described in U.S. Pat. No. 4,963,557.

4-Amino-1-benzylpiperidine, lithium aluminum hydride and tropinone were purchased from the Aldrich Chemical Co. (Milwaukee, Wis.). 3R-Pyrrolidine and 3S-pyrrolidine were purchased from CTC Organics (Atlanta, Ga.).

EXAMPLE 1

2-[4-Piperidinyl]-8,8-dipropyl-2-azaspiro-[4.5]-decane dihydrochloride

(i)
2-[4-(N-Benzyl)piperidinyl]-8,8-dipropyl-2-azaspiro-[4.5]-decane-1,3-decane To a solution of 4,4-dipropylcyclohexane-1-carboxy-1-acetic acid anhydride (1 molar equivalent) in xylene was added 4-amino-1-benzylpiperidine (1 molar equivalent). The reaction mixture was heated at reflux with a Dean-Stark trap until 1 equivalent of water was collected in the trap. The reaction mixture was cooled to room temperature and concentrated under reduced pressure to give a white solid. The crude imide was dissolved in excess ethyl acetate followed by two washes with saturated aqueous sodium bicarbonate solution to remove any residual acid-amide from the product. The organic phase was dried over sodium sulfate, filtered, and concentrated to give the desired imide as a white solid; mp 148°–149° C.; 90–95% yield.

(ii)
2-[4-(N-Benzyl)piperidinyl]-8,8,-dipropyl-2-azaspiro-[4.5]-decane To a mixture of lithium aluminum hydride (3.2 molar equivalents) in tetrahydrofuran was added dropwise a solution of 2-[4-(N-benzyl)piperidinyl]-8,8-dipropyl- 2-azaspiro-[4.5]-decane -1,3-dione (1 molar equivalent) in tetrahydrofuran. The reaction mixture was stirred for 2–6 h following completion of addition. The excess hydride was quenched with sodium sulfate-decahydrate and the resulting mixture was filtered and the filtrate was concentrated to give the desired diamine as a viscous, colorless oil. The oil was used directly without further purification; yield 90–95%.

(iii) 2-(4-Piperidinyl)-8,8-dipropyl-2-azaspiro-[4.5]-decane

To a suspension of 10% palladium-on-carbon (0.1 molar equivalents) in a 7.5% formic acid in methanol solution was added 2-[4-(N-benzyl)piperidinyl]-8,8-dipropyl-2-azaspiro[4.5]-decane (1 molar equivalent). The reaction mixture was hydrogenated at 60 psi hydrogen pressure in a Parr hydrogenation apparatus at room temperature until hydrogen uptake had ceased (48–96 h). The catalyst was removed by filtration through celite and the filtrate concentrated under reduced pressure. The residue was dissolved in water and then basified with 10% NaOH. The resulting aqueous emulsion was extracted with ethyl ether. The organic phase was dried over sodium sulfate, filtered and concentrated to give the debenzylated diamine product as a colorless oil; 90–95% yield.

(iv) 2-(4-Piperidinyl)-8,8-dipropyl-2-azaspiro-[4.5]-decane dihydrochloride 2-(4-Piperidinyl)-8,8-dipropyl-2-azaspiro[4.5]-decane was dissolved in a minimum of anhydrous ethanol and added to a cooled solution of hydrogen chloride in ethanol. On addition of a large volume of ether, a white precipitate formed which was isolated by filteration. The white solid was recrystallized from ethanol or methanol; mp 298°–300° C.; yield 85–90%.

EXAMPLE 2

2-(4-(N-Methyl)piperidinyl)-8,8-dipropyl-2-azaspiro-[4.5]-decane dihydrochloride

(i)
2-(4-(N-Methyl)piperidinyl-8,8-dipropyl-2-azaspiro-[4.5]-decane

To a solution of 2-(4-piperidinyl)-8,8-dipropyl-2-azaspiro[ 4.5]-decane (1 molar equivalent prepared according to Example 1 (iii)) in acetonitrile was added 37% aqueous formaldehyde (5 molar equivalents) and sodium cyanoborohydride (1.6 molar equivalents). The reaction mixture was stirred overnight at room temperature. Added 2N KOH and extracted the reaction mixture twice with ethyl acetate. The combined organic extracts were washed with brine, dried over sodium sulfate, filtered and concentrated to give a yellow viscous oil. The residue was purified by chromatography on silica gel using MeOH/ethyl acetate/conc. ammonium hydroxide (74/24/1.5) as eluant. The product was isolated as a colorless oil; yield 60%.

(ii) 2-(4-N-Methyl)piperidinyl-8,8-dipropyl-2-azaspiro[4.5]-decane dihydrochloride The title compound is prepared according to Example 1 (iv) by substituting 2-(4-(N-Methyl)piperidinyl-8,8-dipropyl-2-azaspiro-[4.5]-decane for 2-(4-Piperidinyl)- 8,8-dipropyl-2-azaspiro[4.5]-decane; mp 332°–334° C.

EXAMPLE 3

2-(4-piperidinyl)-8,8-diethyl-2-azaspiro[4.5]-decane dihydrochloride

The title compound is prepared according to Example 1 (i–iv) by substituting 4,4-diethylcyclohexane-1-carboxy-1-acetic acid anhydride for 4,4-dipropylcyclohexane-1-carboxy-1-acetic acid anhydride; mp 331°–332° C.

EXAMPLE 4

2-(2-(4-Imidazolyl)ethyl)-8,8-dipropyl-2-azaspiro-[4.5]decane dihydrochloride

(i)
2-(2-(4-Imidazolyl)ethyl)-8,8-dipropyl-2-azaspiro-[4.5]decane

The title compound is prepared according to Example 1 (i–iii) by substituting histamine for 4-amino-1-benzylpiperidine.

(ii)
2-(2-(4-Imidazolyl)ethyl)-8,8-dipropyl-2-azaspiro-[4.5]decane dihydrochloride 2-(2-(4-Imidazolyl)ethyl)-8,8-dipropyl-2-azaspiro[ 4.5]decane was dissolved in a minimum amount of ethanol and a solution of $HCl_{(g)}$/EtOH was added. The dihydrochloride did not precipitate. The solution was concentrated to dryness and placed in a vacuum oven overnight at 60°/5 mm to give the desired dihydrochloride salt as a white solid: yield 72%; m.p. 258°–262° C.

EXAMPLE 5

2-(3R-pyrrolidinyl)-8,8-dipropyl-2-azaspiro[4.5]-decane dimaleate (i) 2-(3R-pyrrolidinyl)-8,8-dipropyl-2-azaspiro-[4.5]-decane-1,3-dione To a solution of 4,4-dipropylcyclohexane-1-carboxy-1-acetic acid anhydride (1 molar equivalent) in xylene was added 3R-aminopyrrolidine (1 molar equivalent). The reaction mixture was heated at reflux with a Dean-Stark trap until 1 equivalent of water was collected in the trap. The reaction mixture was cooled to room temperature and concentrated under reduced pressure to give a viscous, dark brown oil. The crude product was dissolved in methanol and a methanol solution containing maleic acid (1 molar equivalent) was added. The volatiles were stripped off under reduced pressure from the product-maleate solution to yield a dark brown solid. The solid was recrystallized from dichloromethane/ethyl acetate to afford the pure salt as a white crystalline solid. The product salt was solubilized in a minimum of water and the resulting solution basified with 1M sodium hydroxide and extracted with ethyl ether. The ether extracts were combined, dried over sodium sulfate, filtered, and concentrated to give the desired imide as a viscous oil; 70–75% yield.

(ii) 2-(3R-pyrrolidinyl)-8,8-dipropyl-2-azaspiro-[4,5]-decane

To a mixture of lithium aluminum hydride (3.2 molar equivalents) in ethyl ether was added dropwise a solution of 2-(3R-pyrrolidinyl)-8,8-dipropyl-2-azaspiro[4.5]-decane-1,3-dione (1 molar equivalent) in ethyl ether. The reaction mixture was stirred for 2–6 h after addition was completed. The excess hydride was quenched with sodium sulfate-decahydrate and the resulting mixture was filtered. The filtrate was concentrated under reduced pressure to give the diamine as a viscous, colorless oil; 80–85% yield.

(iii) 2-(3R-pyrrolidinyl)-8,8-dipropyl-2-azaspiro-[4.5]-decane dimaleate 2-(3R-pyrrolidinyl)-8,8-dipropyl-2-azaspiro-[4.5]-decane was dissolved in methanol and a methanol solution containing maleic acid (2 molar equivalents) was added. The solvent volume was reduced under vacuum. A 10% hexane in ethyl acetate solution was carefully added to the product-methanol solution to form a white precipitate which was isolated by filtration. The white solid product required no further purification, mp 168.5°–170° C.; 70–80% yield.

EXAMPLE 6

2-(3S-pyrrolidinyl)-8,8-dipropyl-2-azaspiro[4.5]-decane dimaleate

The title compound is prepared according to Example 5 (i–iii) by substituting 3S-aminopyrrolidine for 3R-aminopyrrolidine; mp 169.5°–170.5° C.

EXAMPLE 7

2-(3'-Quinuclidinyl)-8,8-dipropyl-2-azaspiro-[4.5]-decane dihydrochloride (i) 2-(3'-Quinuclidinyl)-8,8-dipropyl-2-azaspiro-[4.5]decane-1,3-dione To a solution of 4,4-dipropylcyclohexane-1-carboxy-1-acetic acid anhydride (1 molar equivalent) in toluene was added 3-aminoquinuclidine (1 molar equivalent). The reaction mixture was heated to reflux with stirring using a Dean-Stark trap until the volume of water collected was unchanged (approximately five hours), and then allowed to cool. The toluene was evaporated under reduced pressure and the residue partitioned between ethyl acetate and 1N sodium hydroxide solution. The organic phase was separated, washed with water, dried (MgSO$_4$) and evaporated to give 2-(3-quinuclidinyl)-8,8-dipropyl-2-azaspiro[4.5]decane-1,3-dione (94%) as a yellow oil which solidified on standing. This was used without further purification.

(ii) 2-(3'-Quinuclidinyl)-8,8-dipropyl-2-azaspiro-[4.5]decane

To a stirred suspension of lithium aluminum hydride (3.5 molar equivalents) in the THF (80 ml) at 0° C. under argon was added a solution of 2-(3'-quinuclidinyl)-8,8-dipropyl-2-azaspiro-[4.5]-decane-1,3-dione (1 molar equivalent) in THF dropwise over 45 minutes. The reaction mixture was allowed to warm to room temperature then stirred overnight. Sodium sulfate decahydrate was added slowly in portions to quench the unreacted LAH and the resulting suspension of solids was filtered and the filtrate evaporated under reduced pressure to yield a residual colorless oil.

(iii) 2-(3'-Quinuclidinyl)-8,8-dipropyl-2-azaspiro-[4.5]decane dihydrochloride 2-(3'-Quinuclidinyl)-8,8-dipropyl-2-azaspiro[4.5]decane was dissolved in a small volume of ethanol and a solution of saturated hydrogen chloride in ethanol was added. Upon addition of a large volume of ether a white precipitate formed which was filtered and dried giving the title compound (yield 70%) as a white amorphous solid; mp 277°–278° C. Elemental analysis suggest that the title compound was isolated as the monohydrate.

EXAMPLE 8

2-(3'-α-(8'-Methyl-8-azabicyclo(3.2.1)-8,8-dipropyl-2-azaspiro[4.5]decane dihydrochloride (i) 3-α-Amino-8-methyl-8-azabicyclo(3.2.1)octane (3-a-aminotropane)

A solution of tropinone (5.0 g) in ethanol containing palladium on activated carbon (10%, 2.0 g) was saturated with ammonia at 0° C. then hydrogenated on a Parr apparatus at 50 psi for 24 hours. The mixture was filtered through celite and evaporated under reduced pressure. The colorless residual oil was used without further purification.

The above amine (0.5 g) in methanol (5 ml) was treated with 1 ml of phenyl isothiocyanate. After stirring for 30 minutes and triturating with ether, a crystalline solid precipitated which was filtered off and recrystallized from ethyl acetate. The thioureide melted at 156°–157° C. (A. Stoll, E. Tucker and A. Ebnother, Helv. Chim. Acta 38, 559 (1955) and S. Archer, T. R. Lewis and M. J. Unser, J. Am. Chem.

Soc. 79, 4194 (1957) report melting points of the endo thioureide as 153°–154° C. and 160°–161° C., respectively.)

(ii) 3-β-Amino-8-methyl-8-azabicyclo(3.2.1)octane (3β-aminotropane)

Prepared by sodium/amyl alcohol reduction of tropinone oxime (M. S. Hadley and F. D. King U.S. Pat. No. 4,273,778 for exact procedures).

The corresponding β-aminotropane thioureide melted at 178°–179° C. (R. Willstatler and W. Moller Ber., 31, 1202 (1898) and S. Arther, T. R. Lewis and M. J. Unser, J. Am. Chem. Soc. 79, 4194 (1957) report melting points of 171°–172° C. and 173°–175° C., respectively).

(iii) 2-(3'-α-(8'-Methyl-8'-azabicyclo(3.2.1)-octane)- 8,8-dipropyl-2-azaspiro[ 4.5]decane dihydrochloride The title compound is prepared according to Example 7 (i–iii) by substituting 3-β-Amino-8-methyl-8-azabicyclo-( 3.2.1) octane (3β-aminotropane) for 3-aminogainaclidine. The dihydrochloride was isolated as described in Example 7(iii); yield 60% as a white amorphous solid; m.p. 234°–235° C. in 60% yield. Elemental analyses suggest that the title compound was isolated as the monohydrate.

EXAMPLE 9

2-(3'β-8'-Methyl-8'-azabicyclo(3.2.1)octane)-8,8-dipropyl-2-azaspiro[ 4.5]decane-dihydrochloride The title compound is prepared according to Example 1 (i–iv) by substituting 3-β-aminotropane for 3-α-aminotropane. The dihydrochloride was isolated as a white amorphous solid; m.p. 245°–247° C. Elemental analyses suggest that the title compound was isolated as the monohydrate.

EXAMPLE 10

2-(4-Piperidinyl)-9,9-dipropyl-3-azaspiro[4,5]-decane dihydrochloride

The title compound is prepared according to Example 1 (i–iv) by substituting 4,4-dipropylcyclohexane-1,1-diacetic acid anhydride for 4,4-dipropylcyclohexane-1-carboxy-1-acetic acid anhydride.

II. Composition Examples

EXAMPLE 1—CAPSULE COMPOSITION

An oral dosage form for administering Formula (I) compounds is produced by filing a standard two piece hard gelatin capsule with the ingredients in the proportions shown in Table I, below.

TABLE I

| INGREDIENTS | AMOUNTS |
| --- | --- |
| 8,8-dipropyl-2-azaspirol[4,5]decane-2-(4-piperidine) dihydrochloride | 25 mg |
| Lactose | 55 mg |
| Talc | 16 mg |
| Magnesium Stearate | 4 mg |

EXAMPLE 2—INJECTABLE PARENTERAL COMPOSITION

An injectable form for administering Formula (I) compounds is produced by stirring 1.5% by weight of 8,8-dipropyl-2-azaspiro[ 4,5]decane-2-(4-piperidine) dihydrochloride in 10% by volume propylene glycol in water.

EXAMPLE 3—Tablet Composition

The sucrose, calcium sulfate dihydrate and Formula (I) compound shown in Table II below, are mixed and granulated in the proportions shown with 10% gelatin solution. The wet granules are screened, dried, mixed with the starch, talc and stearic acid, screened and compressed into a tablet.

TABLE II

| Ingredients | Amounts |
| --- | --- |
| 8,8-dipropyl-2-azaspiro[4,5]decane-2-(4-piperidine) dihydrochloride | 20 mg |
| Calcium sulfate dihydrate | 30 mg |
| sucrose | 4 mg |
| starch | 2 mg |
| talc | 1 mg |
| stearic acid | 0.5 mg |

While the above descriptions and examples fully describe the invention and the preferred embodiments thereof, it is understood that the invention is not limited to the particular disclosed embodiments coming within the scope of the following claims.

What is claimed is:

1. A method of treatment of hyperlipidemia in a mammal in need thereof which comprises administering to such mammal an effective amount therefor of a compound of the formula

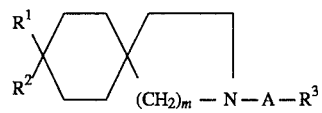

in which:

m is 1 or 2;

$R^1$ and $R^2$ are the same or different and are selected from hydrogen or straight or branched chain alkyl, provided that the total number of carbon atoms contained by $R^1$ and $R^2$ when taken together is 4–10; or $R^1$ and $R^2$ together form a cyclic alkyl group containing 3–7 carbon atoms;

A is absent or present as $C_1$–$C_7$ alkyl; and $R^3$ is a heterocyclic or heterobicyclic ring, said heterocyclic or heterobicyclic ring thereby containing up to 10 carbon atoms and from 1–3 heteroatoms of the formula >$NR^4$, where $R^4$ is absent or present as hydrogen, or a straight chain alkyl containing 1–3 carbon atoms;

or a pharmaceutically acceptable salt, hydrate or solvate thereof.

2. The method of claim 1 wherein the compound is 8,8-dipropyl-2-azaspiro[ 4,5]decane-2-(4-piperidine); or a pharmaceutically acceptable salt, hydrate or solvate thereof.

3. The method of claim 1 wherein the mammal is afflicted with atherosclerosis.

4. The method of claim 1 wherein the mammal is afflicted with transplant arteriolosclerosis.

5. The method of claim 1 wherein the mammal is in need of lower cholesterol and triglyceride levels.

6. The method of claim 1 wherein the mammal is in need of lower cholesterol levels.

7. The method of claim 1 wherein the mammal is in need of lower trigylceride levels.

8. The method of claim 1 wherein the mammal is in need of lower low-density lipoprotein levels.

9. The method of claim 1 wherein the compound is administered orally.

10. The method of claim 9 wherein from about 0.01 mg/kg to about 10 mg/kg of compound is administered per day.

11. The method of claim 1 wherein the compound is administered parenterally.

12. The method of claim 11 wherein from about 0.01 mg/kg to about 10 mg/kg of compound is administered per day.

* * * * *